United States Patent
Paltieli

(10) Patent No.: US 9,554,828 B2
(45) Date of Patent: Jan. 31, 2017

(54) BIRTH DELIVERY DEVICE WITH POSITION SENSOR

(75) Inventor: Yoav Paltieli, Haifa (IL)

(73) Assignee: Trig Medical Ltd., Nesher (IL)

( * ) Notice: Subject to any disclaimer, the term of this patent is extended or adjusted under 35 U.S.C. 154(b) by 303 days.

(21) Appl. No.: 13/395,446

(22) PCT Filed: Sep. 13, 2010

(86) PCT No.: PCT/US2010/048574
§ 371 (c)(1),
(2), (4) Date: Mar. 11, 2012

(87) PCT Pub. No.: WO2011/032065
PCT Pub. Date: Mar. 17, 2011

(65) Prior Publication Data
US 2012/0172890 A1    Jul. 5, 2012

Related U.S. Application Data

(60) Provisional application No. 61/241,906, filed on Sep. 13, 2009.

(51) Int. Cl.
*A61B 17/42* (2006.01)
*A61B 17/44* (2006.01)

(52) U.S. Cl.
CPC ............ *A61B 17/442* (2013.01); *A61B 17/44* (2013.01); *A61B 34/20* (2016.02); *A61B 17/42* (2013.01); *A61B 2034/102* (2016.02)

(58) Field of Classification Search
CPC ... A61B 17/442; A61B 19/5244; A61B 17/42; A61B 17/44; A61B 2019/5259
USPC ................................ 606/119, 122, 123, 205
See application file for complete search history.

(56) References Cited

U.S. PATENT DOCUMENTS

| | | | |
|---|---|---|---|
| 5,578,043 A * | 11/1996 | Galstian ................... | 606/119 |
| 6,200,279 B1 * | 3/2001 | Paltieli ................ | A61B 5/1076 600/426 |
| 6,355,047 B1 * | 3/2002 | Wallace et al. ............... | 606/123 |
| 6,425,899 B1 * | 7/2002 | Biehl ............................ | 606/122 |
| 7,207,996 B2 * | 4/2007 | Burbank et al. .............. | 606/151 |

(Continued)

FOREIGN PATENT DOCUMENTS

FR    2858406    2/2005

OTHER PUBLICATIONS

Moreau, R. et al. (Jul. 2007). "Design of a New Instrumented Forceps: Application to Safe Obstetrical Forceps Blade Placement". IEEE Transactions on Biomedical Engineering, vol. 54, No. 7, pp. 1280-1290.*

(Continued)

Primary Examiner — Diane Yabut
(74) Attorney, Agent, or Firm — Dekel Patent Ltd.; David Klein

(57) ABSTRACT

A birth delivery device (10, 30) including one or more engaging elements (18, 32) shaped to engage a fetal head, one or more handles (19, 40) connected to the one or more engaging elements (18, 32) that manipulate the one or more engaging elements (18, 32), and one or more position sensors (20) placed on a portion of at least one of the engaging elements (18, 32) and the handles (19, 40), the position sensors (20) being in communication with a processor (22) that processes data from the position sensors (20) to determine positional information related to the fetal head.

5 Claims, 2 Drawing Sheets

(56) References Cited

U.S. PATENT DOCUMENTS

| | | |
|---|---|---|
| 7,717,312 B2* | 5/2010 | Beetel .................... 227/175.1 |
| 2003/0114779 A1 | 6/2003 | Paltieli |
| 2003/0163142 A1* | 8/2003 | Paltieli et al. ............... 606/130 |
| 2003/0229267 A1* | 12/2003 | Belson et al. ............... 600/109 |
| 2007/0062301 A1 | 3/2007 | Dittmar et al. |
| 2008/0234581 A1 | 9/2008 | Paltieli |

OTHER PUBLICATIONS

PCT Written Opinion PCT/US2010/048574.
European Search Report EP 10754639.2, dated Mar. 19, 2013.

* cited by examiner

BIRTH DELIVERY DEVICE WITH POSITION SENSOR

CROSS-REFERENCE TO RELATED APPLICATIONS

This application claims priority under 35 USC §119 to U.S. provisional patent Application Ser. No. 61/241906, filed Sep. 13, 2009. and is a national phase application of PCT/US2010/048574, filed Sep. 13, 2010.

FIELD OF THE INVENTION

The present invention relates to birth delivery devices, such as forceps and vacuum extractors, and particularly to such devices with an added position sensor.

BACKGROUND OF THE INVENTION

A number of other physiological conditions of the mother and baby during labor can be monitored in order to determine the progress of labor. These conditions include: (1) effacement (the thinning out of the cervix that occurs before and during the first stage of labor); (2) cervical dilatation (the increase in size of the cervical opening); (3) position of the cervix (the relation of the cervix to the vaginal axis, normally the fetal head); (4) station (the level of a predetermined point of the fetal presenting part with reference to the mother's pelvis), (5) position of the head which describes the relationship of the head to the pelvis and (6) and presentation which describes the part of the fetus (such as brow, face or breech) at the cervical opening.

Systems and methods have been proposed for monitoring the progress of labor. For example, U.S. Pat. Nos. 6,200,279 and 6,669,653 to Paltieli, incorporated herein by reference in their entirety, describe methods and apparatus for monitoring the progress of labor. In one embodiment, the progress of labor is monitored by attaching a position sensor to a predetermined point on the mother's pelvic bones, monitoring the location of the position sensor in three-dimensional space relative to a reference, and monitoring the location of the fetal presenting part with respect to the predetermined point on the mother's pelvic bones. The location of the fetal presenting part may be indicated by a similar position sensor, or by imaging. Other conditions, such as effacement, cervical dilatation, and cervical position may also be monitored in a similar manner.

SUMMARY OF THE INVENTION

The present invention seeks to provide novel birth delivery devices, such as forceps and vacuum extractors, which include one or more position sensors thereon for monitoring the position of the birth delivery device and which may also assist in monitoring the progress of labor, as is described more in detail hereinbelow.

There is provided in accordance with an embodiment of the present invention a birth delivery device including one or more engaging elements shaped to engage a fetal head, one or more handles connected to the one or more engaging elements that manipulate the one or more engaging elements, and one or more position sensors placed on a portion of at least one of the engaging elements and the handles, the position sensors being in communication with a processor that processes data from the position sensors to determine positional information related to the fetal head.

In accordance with an embodiment of the present invention the birth delivery device is an obstetrical forceps and the one or more engaging elements are forceps blades.

In accordance with an embodiment of the present invention the birth delivery device is a vacuum extractor and the one or more engaging elements are a cup.

In accordance with an embodiment of the present invention the one or more position sensors include absolute position sensors.

In accordance with an embodiment of the present invention the one or more position sensors include relative displacement sensors.

In accordance with an embodiment of the present invention the one or more position sensors include sensors for tracking linear and angular movements.

In accordance with an embodiment of the present invention the one or more position sensors include at least one of inductive non-contact position sensors, accelerometers, linear variable differential transformers (LVDTs), capacitive position sensors, eddy-current sensors, Hall effect sensors, optical proximity sensors, piezo-electric transducers, photodiode arrays, magnetic position sensors and ultrasonic sensors.

There is also provided in accordance with an embodiment of the present invention a method for monitoring birth delivery including using a birth delivery device described herein to engage a fetal head and perform birth delivery, and monitoring positional information related to the fetal head by processing data received from the one or more position sensors.

BRIEF DESCRIPTION OF THE DRAWINGS

The invention is herein described, by way of example only, with reference to the accompanying drawings, wherein.

DETAILED DESCRIPTION OF THE INVENTION

Figure 1:
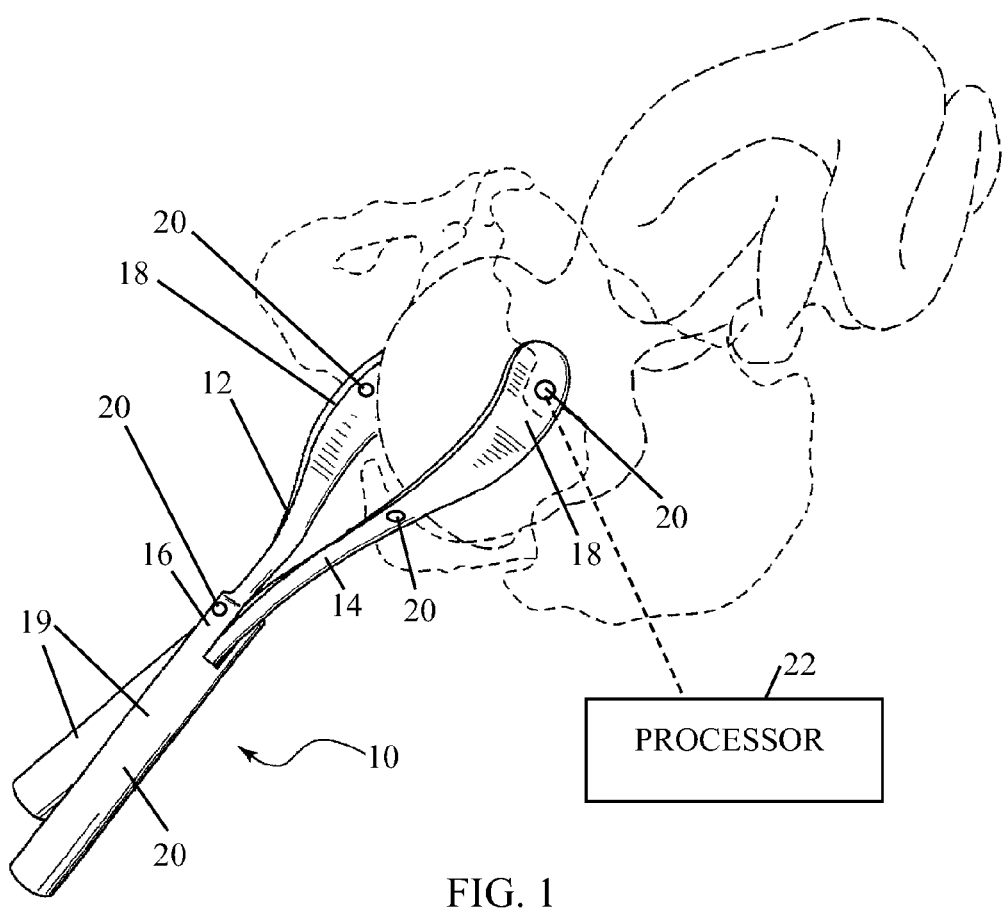
FIG. 1 is a pictorial illustration of a birth delivery device, constructed and operative in accordance with an embodiment of the present invention.

Reference is now made to FIG. 1, which illustrates a birth delivery device 10, constructed and operative in accordance with an embodiment of the present invention.

Birth delivery device 10 is an obstetrical forceps 10, shown engaging a fetal head for assisting delivery. Birth delivery device 10 (or forceps 10) includes a pair of elongate members 12 and 14, pivotally connected to each other at a joint 16 along the length of the members to form what is commonly known as a cross-type forceps. (The invention is not limited to this type of forceps.) Forceps blades 18 (engaging elements) are at the distal ends of elongate members 12 and 14 for grasping the fetal head. Handles 19 are at the proximal ends of elongate members 12 and 14.

In accordance with an embodiment of the present invention, one or more position sensors 20 are mounted to a known point on a portion of forceps 10, such as but not limited to, the forceps blades 18 (on the inside or outside thereof), any portion of elongate members 12 and 14, even handles 19, and any combination thereof.

Position sensor 20 (also referred to as positional tracking sensor 20) may be an absolute position sensor or a relative one (displacement sensor). Position sensor 20 can be either linear or angular for tracking linear and angular movements. Non-limiting examples of position sensors for carrying out the invention include inductive non-contact position sensors, accelerometers, linear variable differential transformers (LVDTs), capacitive position sensors, eddy-current sensors, Hall effect sensors, optical proximity sensors, piezo-electric transducers, photodiode arrays, magnetic position sensors (such as the 3D positional trackers manufactured by Ascension Technology Corporation, Burlington, Vt., US, under the model names MicroBIRD and PcBIRD or PciBIRD), and ultrasonic sensors (such as the microphone/ultrasound position sensor system of Science Accessories Corporation of New Haven, Conn., USA), and any combination thereof.

Position sensors 20 are in communication (wired or wireless) with a processor 22 that processes data from the sensors to determine and display positional information related to the fetal head to aid the medical practitioner in the birth delivery. Processing the positional data may be carried out as is known from the same inventor's U.S. Pat. Nos. 6,200,279 and 6,669,653. Processor 22 may also process positional data from other sensors, such as position sensors mounted on the fetal head and anatomy of the mother (e.g., the maternal pelvis or cervical region), as taught in U.S. Pat. Nos. 6,200,279 and 6,669,653, for monitoring the position of the birth delivery device and for monitoring the progress of labor.

In a preferred embodiment, position sensors 20 are positioned at a known point on the forceps blades 18 (which are preferably rigid). The 3D geometry of the forceps 10 is known to processor 22, either by previously inputting the geometry or sensing it in real time with other position sensors (e.g., by touching other points of the forceps, such as the distal most point of the forceps or other points, with position sensors and using well-known digitizing techniques). The processor 22 identifies the spatial position of the forceps 10 with respect to the maternal pelvis and to the fetal head in six degrees of freedom. This enables the user to guide the forceps 10 for proper engagement with the fetal head.

After the controller identifies that the forceps blades 18 are placed over the fetal head (by knowing the head and the forceps spatial position), the controller (processor 22) calculates the previously determined position of the fetal head and birth canal relative to sensors 20, and the spatial positions and movements of forceps 10 and the fetal head can be displayed simultaneously.

Figure 2:
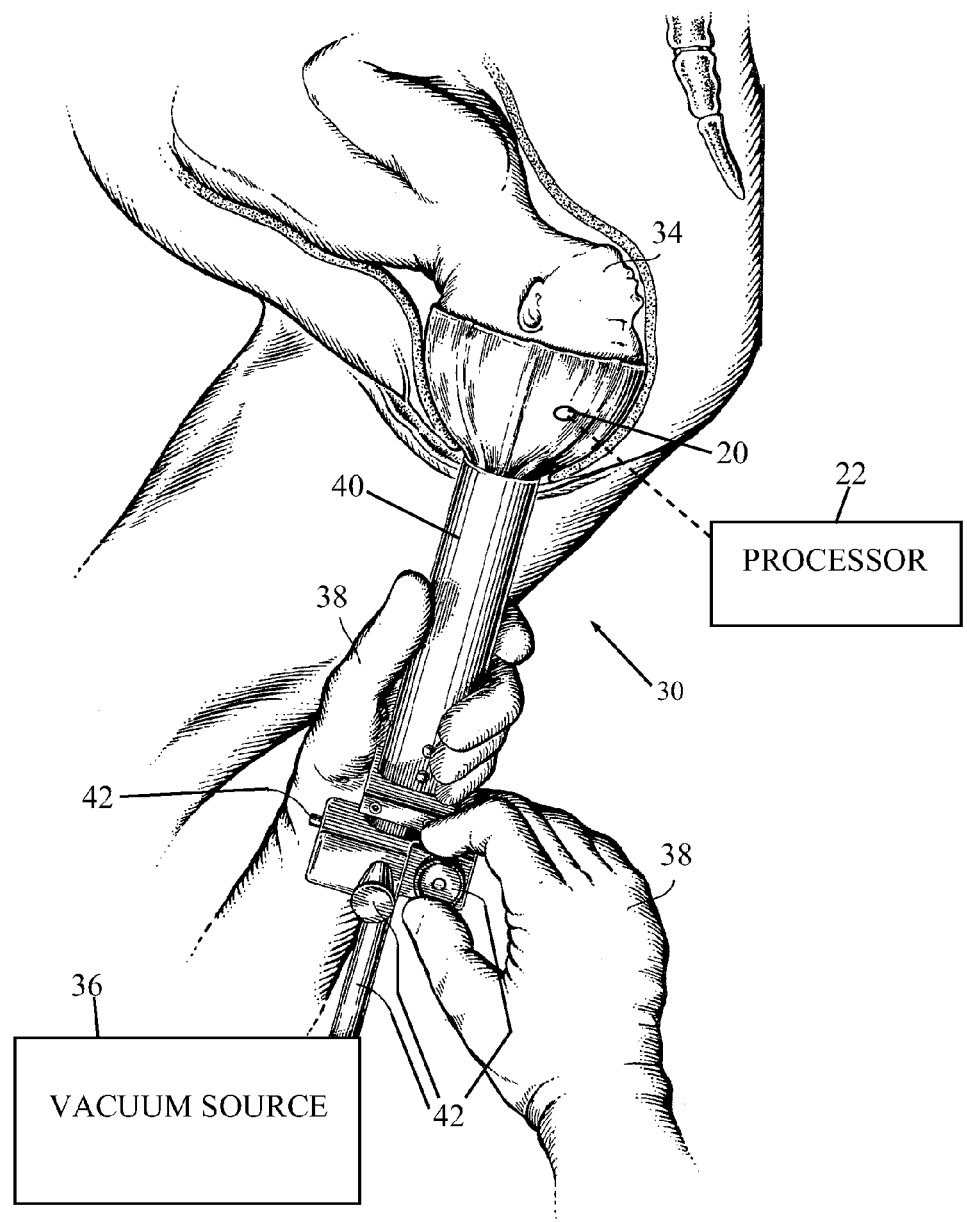
FIG. 2 is a pictorial illustration of a birth delivery device, constructed and operative in accordance with another embodiment of the present invention.

Reference is now made to FIG. 2, which illustrates a birth delivery device 30, constructed and operative in accordance with an embodiment of the present invention.

Birth delivery device 30 is a vacuum extractor (also referred to as vacuum extractor 30), which includes a cup 32 (engaging element), the opening of which is applied to the fetal head 34 after the device has been introduced into the birth canal. Cup 32 is attached to a vacuum source 36 to create a vacuum in cup 32 and thus adhere cup 32 to the fetal head 34. With vacuum extractor 30 adhered to the fetal head 34, the fetus can then be pulled from the birth canal by user 38 manipulating a handle 40 of vacuum extractor 30. Various controls 42 may be provided for controlling the vacuum and other operating parameters.

In accordance with an embodiment of the present invention, one or more position sensors 20 are mounted on a portion of vacuum extractor 30, such as but not limited to, cup 32 (on the inside or outside thereof) or handle 40, and any combination thereof. Position sensors 20 operate as described above.

With vacuum extractor 30, no modeling is normally required as for the forceps. The user can identify the position of the fetal head in the birth canal with the techniques of U.S. Pat. Nos. 6,200,279 and 6,669,653, and engage the fetal head with vacuum extractor 30. Once vacuum extractor 30 is attached properly, the controller (processor 22) calculates the previously determined spatial position of the fetal head and birth canal relative to sensors 20 which moves together with the fetal head, and their positions and movements can be displayed simultaneously.

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

What is claimed is:

1. A birth delivery device comprising:
   one or more fetal head grasping elements configured to grasp a fetal head;
   one or more handles connected to said one or more fetal head grasping elements that manipulate said one or more fetal head grasping elements; and
   one or more position sensors placed on portions of said one or more fetal head grasping elements and said one ore more handles, said one or more position sensors being in communication with a processor that processes data from said one or more position sensors to determine positional information related to said fetal head.

2. The birth delivery device according to claim 1, wherein said birth delivery device is an obstetrical forceps and said one or more fetal head grasping elements are forceps blades.

3. The birth delivery device according to claim 1, wherein said birth delivery device is a vacuum extractor and said one or more fetal head grasping elements is a cup.

4. The birth delivery device according to claim 1, wherein said one or more position sensors comprise at least one of inductive non-contact position sensors, accelerometers, linear variable differential transformers (LVDTs), capacitive position sensors, eddy-current sensors, Hall effect sensors, optical proximity sensors, piezo-electric transducers, photodiode arrays, magnetic position sensors and ultrasonic sensors.

5. A method for monitoring birth delivery comprising using the birth delivery device of claim 1 to grasp a fetal head and using said one or more position sensors to determine positional information related to said fetal head.

* * * * *